(12) United States Patent
Marques Gabriel et al.

(10) Patent No.: US 12,212,376 B2
(45) Date of Patent: Jan. 28, 2025

(54) DETERMINATION OF CAUSE OF DISCONNECTION OF SENSORS OF A MOTION TRACKING SYSTEM

(71) Applicant: SWORD HEALTH S.A., Oporto (PT)

(72) Inventors: Ivo Emanuel Marques Gabriel, Oporto (PT); Márcio Filipe Moutinho Colunas, Oporto (PT); Ivo Jorge Ramos De Magalhães, Oporto (PT); Filipe André Amorim Silva, Oporto (PT); Virgílio António Ferro Bento, Oporto (PT)

(73) Assignee: SWORD HEALTH, S.A.., Oporto (PT)

( * ) Notice: Subject to any disclaimer, the term of this patent is extended or adjusted under 35 U.S.C. 154(b) by 478 days.

(21) Appl. No.: 17/618,637

(22) PCT Filed: Jun. 8, 2020

(86) PCT No.: PCT/EP2020/065846
§ 371 (c)(1),
(2) Date: Dec. 13, 2021

(87) PCT Pub. No.: WO2020/249514
PCT Pub. Date: Dec. 17, 2020

(65) Prior Publication Data
US 2022/0140925 A1 May 5, 2022

(30) Foreign Application Priority Data
Jun. 14, 2019 (EP) ..................................... 19398008

(51) Int. Cl.
*H04B 17/318* (2015.01)
*A61B 5/00* (2006.01)
(Continued)

(52) U.S. Cl.
CPC ......... *H04B 17/318* (2015.01); *A61B 5/0024* (2013.01); *A61B 5/1126* (2013.01);
(Continued)

(58) Field of Classification Search
CPC .... H04B 17/318; H04W 76/10; H04W 84/18; A61B 5/6801; G08B 21/0247; G08B 21/0252; G08B 21/0277; G08B 29/185
See application file for complete search history.

(56) References Cited

U.S. PATENT DOCUMENTS 9,773,401 B1 * 9/2017 Auvenshine ............ H04W 4/38
2015/0094142 A1   4/2015 Stafford
2018/0293861 A1 * 10/2018 Sarkar ................ G08B 13/1427

FOREIGN PATENT DOCUMENTS

EP       3751531  A1   12/2020
EP       3984008  A1    4/2022
(Continued)

OTHER PUBLICATIONS

International Search Report issued Sep. 2, 2020 re: PCT/EP2020/065846, pp. 1-3, citing: US 2015/0094142 A1 and US 2018/0293861 A1.
(Continued)

*Primary Examiner* — Kwang B Yao
*Assistant Examiner* — Bradley D Lytle, Jr.
(74) *Attorney, Agent, or Firm* — SCHWEGMAN LUNDBERG & WOESSNER, P.A.

(57) ABSTRACT

A method for determining cause of a disconnection between a computing device of a motion tracking system and one or more sensors of the system, the sensors arranged on a person's body, the computing device configured to at least receive data through a wireless communications connection. Each sensor is configured to at least transmit data through the connection. The method includes measuring a signal
(Continued)

strength of the connection with each sensor while the communications are established; processing signal strength values corresponding to a sensor when it has been disconnected from the computing device to determine if the sensor has been disconnected due to a distance increase between the person and computing device; and providing or commanding the provision of at least one user perceptible signal when the computing device has determined that at least one sensor has been disconnected due to a distance increase between the person and computing device.

20 Claims, 4 Drawing Sheets

(51) Int. Cl.
    *A61B 5/11*         (2006.01)
    *G08B 21/02*      (2006.01)
    *H04W 76/10*     (2018.01)
    *H04W 84/18*     (2009.01)

(52) U.S. Cl.
    CPC ........ *A61B 5/6801* (2013.01); *G08B 21/0247* (2013.01); *G08B 21/0252* (2013.01); *G08B 21/0277* (2013.01); *H04W 76/10* (2018.02); *H04W 84/18* (2013.01); *A61B 5/7405* (2013.01); *A61B 5/742* (2013.01); *A61B 5/7455* (2013.01); *A61B 2562/0219* (2013.01)

(56) References Cited

FOREIGN PATENT DOCUMENTS

| EP | 3984008 B1 | | 5/2023 |
|----|----|----|----|
| JP | 2017118325 A | * | 6/2017 |
| WO | WO-2020249514 A1 | | 12/2020 |

OTHER PUBLICATIONS

Written Opinion issued Sep. 2, 2020 re: PCT/EP2020/065846, pp. 1-10, citing: US 2015/0094142 A1 and US 2018/0293861 A1.
European Application Serial No. 19398008.3, Extended European Search Report mailed Dec. 2, 2019, 9 pgs.
European Application Serial No. 19398008.3, Noting of loss of rights mailed Jul. 7, 2021, 2 pgs.
International Application Serial No. PCT/EP2020/065846, International Preliminary Report on Patentability mailed Dec. 23, 2021, 12 pgs.

* cited by examiner

DETERMINATION OF CAUSE OF DISCONNECTION OF SENSORS OF A MOTION TRACKING SYSTEM

TECHNICAL FIELD

The present disclosure relates to the field of systems for tracking motion of a person having arranged thereon wearable sensors. More particularly, the disclosure relates to a method for determining whether the cause of a disconnection in wireless communications connections between sensors and a computing device is due to an increase in the distance between the person wearing the sensors and the computing device.

BACKGROUND

Motion tracking or motion capture is becoming a key technique in different applications in which the movement of a target such as a person is an important part in one or more processes of the applications.

Wearable sensors for motion tracking a target may include one or more sensing devices such as gyroscopes, accelerometers, magnetometers, etc. A computing device that is connected to the sensors processes the measurements of one or several of these sensing devices, and determines the movement sequence of the target, at least the movement sequence of the tracked parts of the target (i.e. those with a sensor arranged thereon).

The wireless communications connections between each sensor and the computing device for transmission of data need be in place during the entire motion tracking procedure if the movement sequences are to be provided in real time or almost in real time, which is essential in certain applications. For example, in a physical rehabilitation application, the person and/or the therapist require feedback from the physical exercises done by the person so that corrective action may be taken in the event that the physical exercises are not correctly done, otherwise there is a risk that the person will worsen an injury thereof or cause a further injury.

As the person is wearing the sensors, i.e. has the sensors arranged on a body thereof, the person may for example inadvertently move away from the computing device and lose connection between the computing device and one, some or all sensors due to the limited range of the communications, thereby halting the provision of the movement sequence.

There is an interest in providing a method for determining whether the disconnection between sensors and a computing device is the result of an increase in the distance or gap between the person and the computing device, in which case feedback is to be provided so that the person knows that she/he should get closer to the computing device in order to reestablish the connection. There is also an interest in determining whether a disconnection is about to happen between sensors and the computing device so that the person may take corrective action before the connection is lost, thereby not losing the existing wireless connection(s).

SUMMARY

A first aspect of the disclosure relates to a method for determining cause of a disconnection between a computing device of a motion tracking system and one or more sensors of a plurality of sensors of the motion tracking system, the plurality of sensors being arranged on a body of a person, the computing device being configured to at least receive data through a wireless communications connection and each sensor of the plurality of sensors being configured to at least transmit data through the wireless communications connection, the method comprising:

establishing a wireless communications connection between the computing device and each sensor of the plurality of sensors;

receiving, the computing device, a plurality of packets from each sensor of the plurality of sensors through the respective wireless communications connection;

measuring, the computing device, a signal strength of the wireless communications connection with each sensor of the plurality of sensors while the wireless communications are established;

processing, the computing device, the signal strength values corresponding to a sensor of the plurality of sensors when said sensor has been disconnected from the computing device so as to determine if said sensor has been disconnected from the computing device due to a distance increase between the person and the computing device; and providing or commanding, the computing device, the provision of at least one user perceptible signal when the computing device has determined that at least one sensor of the plurality of sensors has been disconnected from the computing device due to a distance increase between the person and the computing device.

When the computing device establishes the connection with the plurality of sensors, each sensor is capable of wirelessly transmitting packets to the computing device with measurements of one or more sensing devices within each sensor. While the computing device is connected to each sensor for receiving packets therefrom, the computing device measures the strength of the signal for each sensor and stores discrete values thereof in a memory of the computing device. The signal strength values preferably correspond to a received signal strength indicator (RSSI) as known in the art.

When a disconnection event occurs, which is triggered by the protocol managing the wireless communications connection upon detecting that the connection between two devices has been lost, the computing device evaluates the signal strength values for the sensor that has been disconnected from the computing device in order to determine if the cause of the disconnection is that the distance between the person wearing the sensors and the computing device has increased and, thus, the electromagnetic waves do not have enough power to reach the other device so that they may be captured and/or the data recovered. To this end, the computing device evaluates the evolution over time of the signal strength of the connection with said sensor and may determine that the disconnection was caused by the increase in distance between the person and the computing device if there has been a progressive reduction in the signal strength based on the discrete signal strength values.

By processing the signal strength values in a time period during which the sensor and the computing device were connected (preferably a recent time period, i.e. a span of time between a first time instant and a second time instant before the disconnection event occurred, e.g. when the last packet was received), and evaluating whether the signal strength values in that time period dropped more than a predetermined threshold (e.g. predetermined minimum signal strength drop threshold), it is determined that the distance from the person to the computing device increased. By way of example, the first time instant selected for the time period may be a predetermined value such as a time duration going backwards from the second time instant (e.g. 15 seconds, 30 seconds, 60 seconds, etc. before the second time instant), right after establishing the wireless connection, etc.

In the event that a disconnection occurs and the computing device determines that the cause of the same is that the person moved away from the computing device, the computing device provides or commands the provision of one or more user perceptible signals (e.g. visual indications, audible indications, tactile indications such as a vibration) for notifying the person. In this sense, the computing device may be provided with means for providing such user perceptible signals, and/or may communicate with means for providing user perceptible signals that are not part of the computing device (and which may be or may not be part of the motion tracking system), e.g. a screen, audio output means such as loudspeakers, etc. The signal(s) may be indicative of the cause of disconnection, i.e. the person moving such that she/he is now far away from the computing device, and/or indicative of an action to be taken by the person, namely an indication that the person should go towards the computing device so as to reestablish connection.

In some embodiments, the computing device provides or commands the provision of the at least one user perceptible signal when the computing device has determined that some or all sensors of the plurality of sensors have been disconnected from the computing device due to the distance increase between the person and the computing device.

The computing device does not provide or command the provision of the one or more user perceptible signals if it has not determined that at least some (e.g. two, three, or more) or all the sensors have been disconnected due to the distance increase between the person and the computing device; the number of sensors for which such determination shall be made is established by means of a predetermined sensors threshold. In the event that it is determined that one or some sensors, but fewer than the predetermined sensors threshold, have lost connection for this reason, it is considered that the disconnection is due to another phenomenon, e.g. due to a hardware failure, a software error, interferences, etc. This is so because the computing device expects that more sensors lose the connection due to a distance increase between the person and the device owing to the arrangement of the sensors on the body of the person; all the sensors are more or less at a same distance from the computing device and the wireless communications links normally feature similar path-loss conditions. Therefore, in this embodiment, false positive determinations may be avoided.

In some embodiments, when the computing device has determined that at least one sensor of the plurality of sensors has not been disconnected from the computing device due to a distance increase between the person and the computing device, or when the computing device has determined that fewer sensors than a predetermined sensors threshold have been disconnected from the computing device due to the distance increase between the person and the computing device, the computing device carries out at least one of the following:
  providing or commanding the provision of at least one user perceptible signal indicative of: a warning that one or more sensors have lost connection with the computing device, a cause of disconnection being an interference or a malfunction of the motion tracking system, or an indication that the person should attempt a connection reestablishment;
  storing in at least one memory of the computing device a log event of a disconnection; and
  transmitting a notification to a computing apparatus remote from the computing device that is indicative of: a warning that one or more sensors have lost connection with the computing device, or a cause of disconnection being an interference or a malfunction of the motion tracking system.

The person is notified of the existence of a problem in the wireless communications connections so that she/he may attempt to perform a corrective action. Alternatively, the log event stored or the notification to the remote computing apparatus may be used by the supplier of the motion tracking system or operators in charge of the same to investigate and/or troubleshoot the problem.

In some embodiments, the computing device determines that at least one sensor has been disconnected from the computing device due to the distance increase between the person and the computing device when:
  a difference between a first signal strength value measured at a first time instant and a second signal strength value measured at a second time instant is greater than or equal to a predetermined minimum signal strength drop threshold, the first and second signal strength values corresponding to one sensor of the plurality of sensors, the second time instant being posterior to the first time instant, and the second signal strength value being less than the first signal strength value;
  a time elapsed between the first and second time instants is less than or equal to a predetermined maximum signal drop time threshold; and
  a time elapsed between the second time instant and the disconnection between the computing device and the sensor is less than or equal to a predetermined maximum disconnection time threshold.

The difference in signal strength, i.e. the signal strength drop between the first and second time instants, has to exceed the predetermined minimum signal strength drop threshold in a time period with duration not greater than the predetermined maximum signal drop time threshold. Also, in order to establish that such signal strength drop is indicative of the increase in the distance, the drop must have occurred such that a time duration from the second time instant to the time instant at which the disconnection event is triggered is not greater than the predetermined maximum disconnection time threshold. In this way, signal drops occurring much before (relative to the value of the predetermined maximum disconnection threshold) the disconnection event is triggered are not considered for determining that the cause of the disconnection is that there has been an increase in the distance.

In some embodiments, the computing device determines that at least one sensor has been disconnected from the computing device due to the distance increase between the person and the computing device further when the time elapsed between the first and second time instants is greater than or equal to a predetermined minimum signal drop time threshold.

The signal drop should occur when the time elapsed between the first and second time instants is also equal to or greater than the predetermined minimum signal drop time threshold for determining that the cause of the disconnection is that there has been an increase in the distance between the person and the computing device. In this manner, the computing device ignores disconnections due to sporadic phenomena, for example interferences, that could result in false positive determinations.

In some embodiments, the method further comprises:

processing, the computing device, the signal strength values corresponding to a sensor of the plurality of sensors when said sensor is connected to the computing device so as to determine if said sensor may lose connection with the computing device due to the distance increase between the person and the computing device; and providing or commanding, the computing device, the provision of at least one user perceptible signal when the computing device has determined that at least one sensor of the plurality of sensors may lose connection with the computing device due to the distance increase between the person and the computing device.

By processing the signal strength values for each sensor and any possible drop thereof, it is possible to determine whether a disconnection is about to happen (e.g. in 5 seconds, 10 seconds, 20 seconds, 30 seconds, etc.) due to an increase in the distance between the person and the computing device. In that case, the computing device provides or commands the provision of the user perceptible signal(s) so as to warn the person that a disconnection may occur if she/he moves farther away from the computing device, and/or advise the person to get closer to the computing device.

In some embodiments, the computing device provides or commands the provision of the at least one user perceptible signal when the computing device has determined that at least one sensor of the plurality of sensors may lose connection with the computing device due to the distance increase between the person and the computing device.

The computing device may only provide or command the provision of the one or more user perceptible signals when it has determined that at least some or all the sensors may lose connection with the computing device due to the distance increase between the person and the computing device; the number of sensors for which such determination shall be made is established by means of a predetermined sensors threshold.

In some embodiments, the computing device determines that at least one sensor may lose connection with the computing device due to the distance increase between the person and the computing device when:

a difference between a one signal strength value (e.g. first signal strength value, third signal strength value, etc.) measured at one time instant (e.g. first time instant, third time instant, etc.) and another signal strength value (e.g. second signal strength value, fourth signal strength value, etc.) measured at another time instant (e.g. second time instant, fourth time instant, etc.) is greater than or equal to a (or the) predetermined minimum signal strength drop threshold, the one and another signal strength values corresponding to one sensor of the plurality of sensors, the another time instant being posterior to the one time instant, and the another signal strength value being less than the one signal strength value; and a time elapsed between the one and another time instants is less than or equal to a (or the) predetermined maximum signal drop time threshold.

In these embodiments, a predetermined maximum signal strength threshold establishes the maximum value that the signal strength measured by the computing device may have so as to consider that a connection loss may potentially occur. To this end, the computing device compares the most recent signal strength values with the predetermined maximum signal strength threshold and, when at least one value is below said threshold, the computing device processes a recent set of signal strength values so as to determine if the disconnection is about to happen because the distance has increased. This means that, as long as the signal strength values exceed the threshold, the computing device considers that there is no risk of the sensor(s) being about to get disconnected from the computing device.

In some embodiments, the computing device determines that at least one sensor may lose connection with the computing device due to the distance increase between the person and the computing device further when the time elapsed between the one and another time instants is greater than or equal to a (or the) predetermined minimum signal drop time threshold.

In some embodiments, the computing device processes both the signal strength values corresponding to the sensor of the plurality of sensors and orientation measurements included in the packets received from some or all sensors of the plurality of sensors when said sensor has been disconnected from the computing device so as to determine if said sensor has been disconnected from the computing device due to the distance increase between the person and the computing device.

The orientation measurements of the plurality of sensors may reveal that the person with the sensors arranged thereon (e.g. on the front-facing portion of the body) at some point turned around and the person started to face in a direction opposite to where the computing device is, or vice versa. When the person turns around, even if the distance to the computing device does not change, the computing device usually receives the signals from the sensors with lower power because the person partially or completely blocks the line-of-sight between the sensors and the computing device, thereby interfering in the electromagnetic wave propagation. The signal strength is, thus, influenced by the direction the person is facing to relative to the computing device. So, when the person turns about the vertical axis a certain angle, e.g. 55°, 100°, 130°, 180°, etc., the headings of the sensors also vary, thereby making possible to digitally estimate the evolution of the person heading-wise.

When the computing device processes both the signal strength values and the orientation measurements, it may determine whether a reduction in signal strength is caused by a movement of the person going farther away from the computing device or because the person turned around. The computing device derives the heading of the sensors from the orientation measurements, which reveal how the person turned about a vertical axis thereof relative to previous orientation measurements. The computing device thus determines whether the person changes her/his heading during the motion tracking procedure by both processing the heading of some (e.g. two, three, etc.) or all the sensors based on the orientation measurements thereof and digitally evaluating the change in heading in said some or all sensors. By establishing a relationship between the signal strength values and the orientation measurements corresponding to said signal strength values, false positives may be avoided in the determination of whether the cause of disconnection or the cause of a disconnection that may soon occur is due to the distance increase between the person and the computing device.

In some embodiments, the computing device processes both the signal strength values corresponding to the sensor of the plurality of sensors and orientation measurements included in the packets received from some or all sensors of the plurality of sensors (when it has been determined that at least one sensor may lose connection with the computing device) so as to determine if at least one sensor may lose connection with the computing device due to the distance increase between the person and the computing device.

In some embodiments, the computing device determines that at least one sensor has been disconnected from the computing device due to the distance increase between the person and the computing device further when a difference between headings of orientation measurements in respective first and second packets received from the each sensor of the some or all sensors of the plurality of sensors are indicative of the person not having turned more than 90° (or more than any one of: 120°, 135°, and 150°) about a vertical axis thereof, each first and second packets having been received by the computing device from each sensor of the some or all sensors of the plurality of sensors at respective first and second reception time instants for each sensor, respectively, time differences between the first time instant and the first reception time instant of each respective sensor and between the second time instant and the second reception time instant of each respective sensor being less than or equal to a predetermined time difference, the second reception time instant of each respective sensor being posterior to the first reception time instant of each respective sensor.

When the person turns more than 90° to either side thereof about the vertical axis of the person, the signal strength values are reduced due to the occlusions caused by the person itself. Accordingly, the signal strength drop should occur while the person has turned less than 90° to either side thereof to determine that the cause of disconnection is the distance increase.

In one example, the predefined time difference is inversely proportional to a frequency with which the sensors transmit data packets or the computing device measures signal strength, e.g. $K \cdot f^{-1}$, where K is a constant selected in accordance with routine experiments and f is the frequency of data packet transmission or signal strength measurement. In another example, the predefined time difference is selected in accordance with routine experiments, e.g. 1 second, 2 seconds, 5 seconds, etc.

In some embodiments, the computing device carries out the aforementioned processing of both signal strength values and orientation measurements when the respective sensor is connected to the computing device so as to determine if said sensor may lose connection with the computing device due to the distance increase between the person and the computing device.

The computing device evaluates the orientation measurements in some embodiments in which the computing device is to determine whether a possible connection loss may be about to occur due to a signal strength drop in the wireless communications connection between the computing device and a sensor. The computing device assesses whether the reduction in signal strength is due to the distance increase between the person and the computing device, or the person turning about the vertical axis thereof (thereby changing its heading relative to the computing device), thus reducing the number of false positive determinations, the latter being further reduced in some embodiments by requiring that the computing device determines that some or all sensors of the plurality of sensors (in accordance with the predetermined sensors threshold) are about to lose connection due to the aforesaid distance increase.

In some embodiments, the wireless communications connections are Bluetooth communications connections.

In some embodiments, each sensor of the plurality of sensors at least comprises a gyroscope. In some embodiments, each sensor of the plurality of sensors further comprises an accelerometer and/or a magnetometer.

In some embodiments, the computing device is remote from the person.

In some embodiments, the computing device is still.

The computing device is, for example, a tablet, a desktop computer, a laptop computer, etc.

A second aspect of the disclosure relates to a method for determining that a computing device of a motion tracking system and one or more sensors of a plurality of sensors of the motion tracking system may lose connection in established wireless communications connections due to a distance increase between a person with the plurality of sensors arranged on a body thereof and the computing device, the computing device being configured to at least receive data through a wireless communications connection and each sensor of the plurality of sensors being configured to at least transmit data through the wireless communications connection, the method comprising:

establishing a wireless communications connection between the computing device and each sensor of the plurality of sensors;

receiving, the computing device, a plurality of packets from each sensor of the plurality of sensors through the respective wireless communications connection;

measuring, the computing device, a signal strength of the wireless communications connection with each sensor of the plurality of sensors while the wireless communications are established;

processing, the computing device, the signal strength values corresponding to a sensor of the plurality of sensors when said sensor is connected to the computing device so as to determine if said sensor may lose connection with the computing device due to the distance increase between the person and the computing device; and providing or commanding, the computing device, the provision of at least one user perceptible signal when the computing device has determined that at least one sensor of the plurality of sensors may lose connection with the computing device due to the distance increase between the person and the computing device.

By processing the signal strength values for each sensor and any possible drop thereof, it is possible to determine whether a disconnection may occur due to an increase in the distance between the person and the computing device, in which case the computing device warns the person about the potential disconnection and/or advises the person to get closer to the computing device by means of one or more user perceptible signals.

In some embodiments, the computing device provides or commands the provision of the at least one user perceptible signal when the computing device has determined that some or all sensors of the plurality of sensors may lose connection with the computing device due to the distance increase between the person and the computing device.

In some embodiments, the computing device determines that at least one sensor may lose connection with the computing device due to the distance increase between the person and the computing device when: a difference between a first signal strength value measured at a first time instant and a second signal strength value measured at a second time instant is greater than or equal to a predetermined minimum signal strength drop threshold, the first and second signal strength values corresponding to one sensor of the plurality of sensors, the second time instant being posterior to the first time instant, and the second signal strength value being less than the first signal strength value; and a time elapsed between the first and second time instants is less than or equal to a predetermined maximum signal drop time threshold.

In some embodiments, the computing device determines that at least one sensor may lose connection with the computing device due to the distance increase between the person and the computing device further when the time elapsed between the first and second time instants is greater than or equal to a predetermined minimum signal drop time threshold.

In some embodiments, the method further comprises:
processing, the computing device, the signal strength values corresponding to a sensor of the plurality of sensors when said sensor has been disconnected from the computing device so as to determine if said sensor has been disconnected from the computing device due to a distance increase between the person and the computing device; and
providing or commanding, the computing device, the provision of at least one user perceptible signal when the computing device has determined that at least one sensor of the plurality of sensors has been disconnected from the computing device due to a distance increase between the person and the computing device.

In some embodiments, the computing device provides or commands the provision of the at least one user perceptible signal when the computing device has determined that some or all sensors of the plurality of sensors have been disconnected from the computing device due to the distance increase between the person and the computing device.

In some embodiments, when the computing device has determined that at least one sensor of the plurality of sensors has not been disconnected from the computing device due to a distance increase between the person and the computing device, or when the computing device has determined that fewer sensors than a predetermined sensors threshold have been disconnected from the computing device due to the distance increase between the person and the computing device, the computing device carries out at least one of the following:
providing or commanding the provision of at least one user perceptible signal indicative of: a warning that one or more sensors have lost connection with the computing device, a cause of disconnection being an interference or a malfunction of the motion tracking system, or an indication that the person should attempt a connection reestablishment;
storing in at least one memory of the computing device a log event of a disconnection; and
transmitting a notification to a computing apparatus remote from the computing device that is indicative of: a warning that one or more sensors have lost connection with the computing device, or a cause of disconnection being an interference or a malfunction of the motion tracking system.

In some embodiments, the computing device determines that at least one sensor has been disconnected from the computing device due to the distance increase between the person and the computing device when:
a difference between one signal strength value (e.g. first signal strength value, third signal strength value, etc.) measured at one time instant (e.g. first time instant, third time instant, etc.) and another signal strength value (e.g. second signal strength value, fourth signal strength value, etc.) measured at another time instant (e.g. second time instant, fourth time instant, etc.) is greater than or equal to a (or the) predetermined minimum signal strength drop threshold, the one and another signal strength values corresponding to one sensor of the plurality of sensors, the another time instant being posterior to the one time instant, and the another signal strength value being less than the one signal strength value;
a time elapsed between the one and another time instants is less than or equal to a (or the) predetermined maximum signal drop time threshold; and
a time elapsed between the another time instant and the disconnection between the computing device and the sensor is less than or equal to a (or the) predetermined maximum disconnection time threshold.

In some embodiments, the computing device determines that at least one sensor has been disconnected from the computing device due to the distance increase between the person and the computing device further when the time elapsed between the one and another time instants is greater than or equal to a (or the) predetermined minimum signal drop time threshold.

In some embodiments, the computing device determines that at least one sensor may lose connection with the computing device due to the distance increase between the person and the computing device further when a difference between headings of orientation measurements in respective first and second packets received from the each sensor of the some or all sensors of the plurality of sensors are indicative of the person not having turned more than 90° (or more than any one of: 120°, 135°, and 150°) about a vertical axis thereof, each first and second packets having been received by the computing device from each sensor of the some or all sensors of the plurality of sensors at respective first and second reception time instants for each sensor, respectively, time differences between the first time instant and the first reception time instant of each respective sensor and between the second time instant and the second reception time instant of each respective sensor being less than or equal to a predetermined time difference, the second reception time instant of each respective sensor being posterior to the first reception time instant of each respective sensor.

In some embodiments, the computing device carries out the aforementioned processing of both signal strength values and orientation measurements when the computing device has determined that at least one sensor has been disconnected from the computing device so as to determine if said sensor has been disconnected from the computing device due to the distance increase between the person and the computing device.

In some embodiments, the wireless communications connections are Bluetooth communications connections.

In some embodiments, each sensor of the plurality of sensors at least comprises a gyroscope. In some embodiments, each sensor of the plurality of sensors further comprises an accelerometer and/or a magnetometer.

In some embodiments, the computing device is remote from the person.

In some embodiments, the computing device is still.

Similar advantages as those described with reference to the first aspect of the disclosure may also be applicable to this aspect of the disclosure.

A third aspect of the disclosure relates to a motion tracking system comprising:
a plurality of sensors adapted to be arranged on a body of a person; and a computing device comprising means for carrying out steps of a method according to the first aspect of the disclosure, or according to the second aspect of the disclosure;

each sensor of the plurality of sensors comprising a first communications module configured to establish a wireless communications connection and to at least transmit data through the wireless communications connection; and the computing device comprising a second communications module configured to establish a wireless communications connection and to at least receive data through the wireless communications connection.

The motion tracking system is configured to determine whether a disconnection or a possible disconnection that may be about to happen between the computing device and one or more sensors is because the distance between the person and the computing device increased such that the electromagnetic waves cannot travel the distance between the sensors and the computing device so as to reach the device at the other end of the wireless communications connection with enough power to be detected and/or demodulated.

Both the computing device and each sensor of the motion tracking system comprises at least one processor, at least one memory and a communications module for wireless communications. In some embodiments, the communications modules of the sensors are further configured to receive data through the wireless communications connection. In some embodiments, the communications module of the computing device is further configured to transmit data through the wireless communications connection.

In some embodiments, the motion tracking system or the computing device comprises means for providing at least one user perceptible signal, whereas in some other embodiments, the computing device wirelessly communicates with means for providing at least one user perceptible signal that are not part of the motion tracking system. The means may be, for example, a screen, audio output means such as loudspeakers, etc.

A fourth aspect of the disclosure relates to a computer program product that has instructions which, when the program is executed by a computing device, cause the computing device to carry out steps of a method according to the first aspect of the disclosure, or according to the second aspect of the disclosure.

A fifth aspect of the disclosure relates to a data stream which is representative of a computer program product according to the fourth aspect of the disclosure.

A sixth aspect of the disclosure relates to a computer-readable storage medium comprising instructions which, when executed by a computing device, cause the computing device to carry out steps of a method according to the first aspect of the disclosure, or according to the second aspect of the disclosure.

BRIEF DESCRIPTION OF THE DRAWINGS

To complete the description and in order to provide for a better understanding of the disclosure, a set of drawings is provided. Said drawings form an integral part of the description and illustrate embodiments of the disclosure, which should not be interpreted as restricting the scope of the disclosure, but just as examples of how the disclosure can be carried out. The drawings comprise the following figures.

DETAILED DESCRIPTION OF THE DRAWINGS

Figure 1:
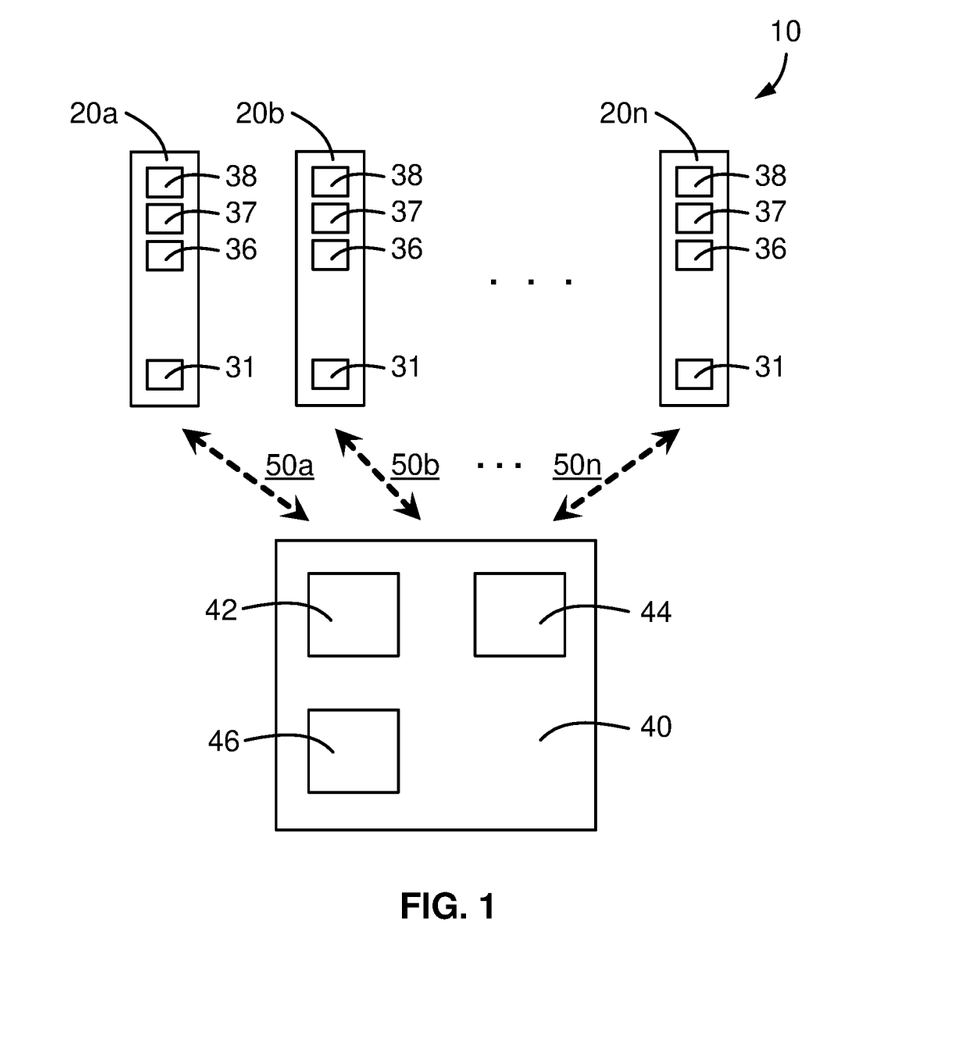
FIG. 1 diagrammatically shows a motion tracking system in accordance with an embodiment.

FIG. 1 diagrammatically shows a motion tracking system 10 in accordance with an embodiment. The motion tracking system 10 includes a plurality of two or more sensors 20a-20n, and a computing device 40.

Each of the sensors 20a-20n includes a sensing device such as a gyroscope 31, but could additionally or alternatively include an accelerometer, and/or a magnetometer. The sensors 20a-20n also include at least one processor 36, at least one memory 37, and a first communications module 38 for wirelessly transmitting data (through a wireless communications technology and protocol known by a skilled person, for instance Bluetooth), the data being transmitted by the sensors 20a-20n in the form of data packets that include one or more measurements; the measurements may be raw measurements of the sensing devices, or measurements already processed by the at least one processor 36 of the sensors 20a-20n (as known in the art, if the sensor is provided with several sensing devices, a sensor fusion algorithm may receive the measurements from the sensing devices in order to provide measurements that, in principle, are more accurate). In some embodiments, the same first communications modules 38 enable the sensors 20a-20n to receive data from other devices, such as from the computing device 40.

The computing device 40 includes at least one processor 42, at least one memory 44, and a second communications module 46 for at least wirelessly receiving data. In some embodiments, the second communications module 46 also enable the computing device 40 to transmit data to other devices.

For illustrative purposes only, dashed lines with arrows represent wireless communications connections 50a-50n established between each sensor 20a-20n and the computing device 40 by means of the respective communications modules 38, 46.

The computing device 40 is configured to measure signal strength of the wireless communications connections 50a-50n. In this sense, the computing device 40 is capable of providing, for instance but without limitation, received signal strength indicators (RSSI) for each connection as known in the art, or received channel power indicators (RCPI) for each connection as known in the art.

Figure 2:
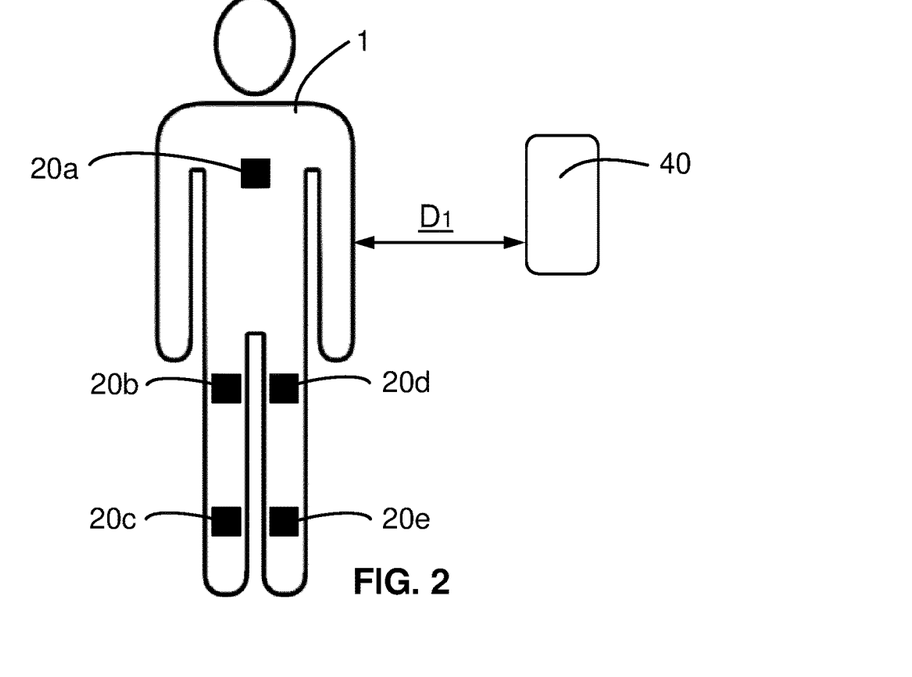
FIGS. 2 and 3 diagrammatically show a person wearing sensors of a motion tracking system at different distances from a computing device of the system.
Figure 3:
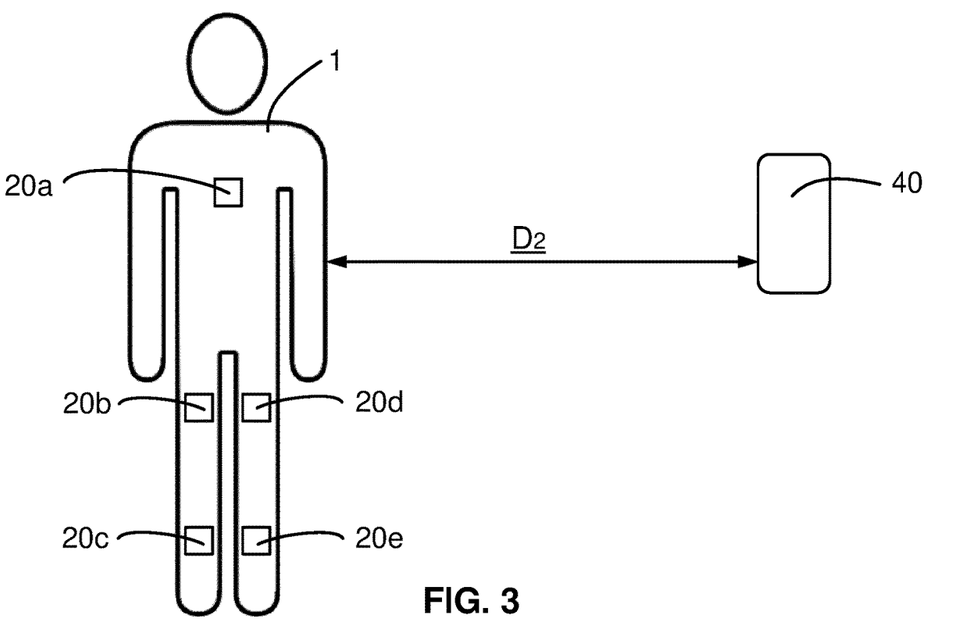

FIGS. 2 and 3 diagrammatically show a person 1 wearing sensors 20a-20e of a motion tracking system (such as motion tracking system 10 of FIG. 1) at different distances from a computing device 40 of the system. The computing device 40 is preferably still, for instance by attachment thereof to a surface of a room or piece of furniture, or while being on a still surface like a table or a tripod. The computing device 40 is remote from the person 1 while the latter performs some physical exercises and the movement thereof is being tracked.

In FIG. 2, the person 1 is at a first distance $D_1$, which is the shortest distance between the person 1 (any body member thereof) and the computing device 40. At said distance, each sensor 20a-20e has established a wireless communications connection with the computing device 40 (as diagrammatically illustrated in FIG. 1 with reference numbers 50a-50n). For illustrative purposes only, the sensors 20a-20e are represented filled with black color to denote that they are wirelessly connected to the computing device 40.

While the sensors are connected to the computing device 40, the person 1 moves and does physical exercises that may have been prescribed to her/him by a therapist or a fitness instructor. In this regard, the person 1 attempts to reproduce the movements or physical exercises so as to rehabilitate from an injury and/or improve her/his physical condition.

The sensors 20a-20e track the motion of the body members having a sensor 20a-20e arranged thereon; they transmit the orientation measurements to the computing device 40, which in turn determines and provides a movement sequence of said body members and, possibly, of other body members with no sensors arranged thereon by means of digital processing of the measurements.

The computing device 40 is capable of digitally comparing the movement sequences with the prescribed movements and/or physical exercises that the person 1 is to reproduce, and provide feedback to the person and/or the therapist or fitness instructor so as to inform whether the same are being correctly performed by the person, or whether the person has not moved one or more body members in accordance with the prescribed movements or exercises. Also, the feedback provided by the computing device 40 may indicate which body members have not been moved correctly and/or provide guidance on how to properly perform the movement or exercise. The motion tracking, the processing by the computing device 40 and the feedback provision are important for the correct rehabilitation and/or improvement of the physical condition of the person because, otherwise, the injury or physical condition of the person 1 may worsen. Also, the computing device 40 may receive (for example wirelessly via an Internet connection provided by a cellular network) input from the therapist or instructor so as to adjust the level of difficulty of the movements/exercises based on the motion tracking and movement sequences provided by the computing device 40; the input may also be in the form of a change in the routine of movements/exercises to be performed by the person 1. The computing device 40 may provide or command the provision of examples and guidance on which movements/exercises are to be performed by the person 1 when activity thereof is to be tracked with the motion tracking system.

As the person 1 performs the movements/exercises, she/he may for instance move away from the computing device 40 as illustrated in FIG. 3; the person 1 perhaps moves away inadvertently, or decides to move to a position in which more room is available for performing the exercises. Regardless of the reason why the person 1 moved, the distance between the person 1 and the computing device 40 increases to a second distance $D_2$, at which the sensors 20a-20e lost the wireless connection with the computing device 40. For illustrative purposes only, the sensors 20a-20e are represented filled with white color to denote that they are not wirelessly connected to the computing device 40 anymore.

The computing device 40 processes the signal strength values that have been measured for each sensor 20a-20e while it was wirelessly connected to each one of them. Accordingly, the computing device 40 processes the evolution in signal strength over time for each sensor since the wireless connection was established up to the moment that the disconnection event has occurred. Therefore, the computing device 40 processes signal strength values that were measured and processed, usually at discrete times, at least from the scenario illustrated in FIG. 2 and at least up to the scenario illustrated in FIG. 3.

The drop in the signal strength values that occurred between the moments of FIG. 2 and FIG. 3 can result in the determination, by the computing device 40, that the cause of disconnection of the sensors 20a-20e from the computing device 40 is due to the increase in the distance, from $D_1$ to $D_2$, between the person 1 and the computing device 40.

Normally, the disconnection event is triggered by the communications protocol used in the wireless communications as known in the art. The communications protocol, such as Bluetooth, is provided with mechanisms for both monitoring the connection between pairs of devices and establishing whether a disconnection between a pair of devices has occurred at some point based on the criteria defined in the protocol; for example, a connection supervision timeout parameter may be defined in the protocol for the protocol to detect the disconnection.

Figure 4:
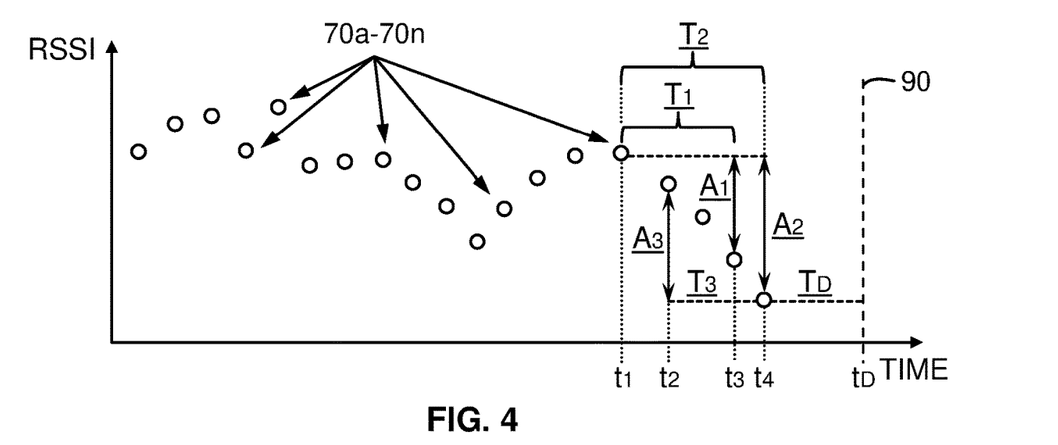
FIGS. 4 and 5 illustrate exemplary charts with measurements by the computing device of signal strength of the wireless communications connection with one sensor.
Figure 5:
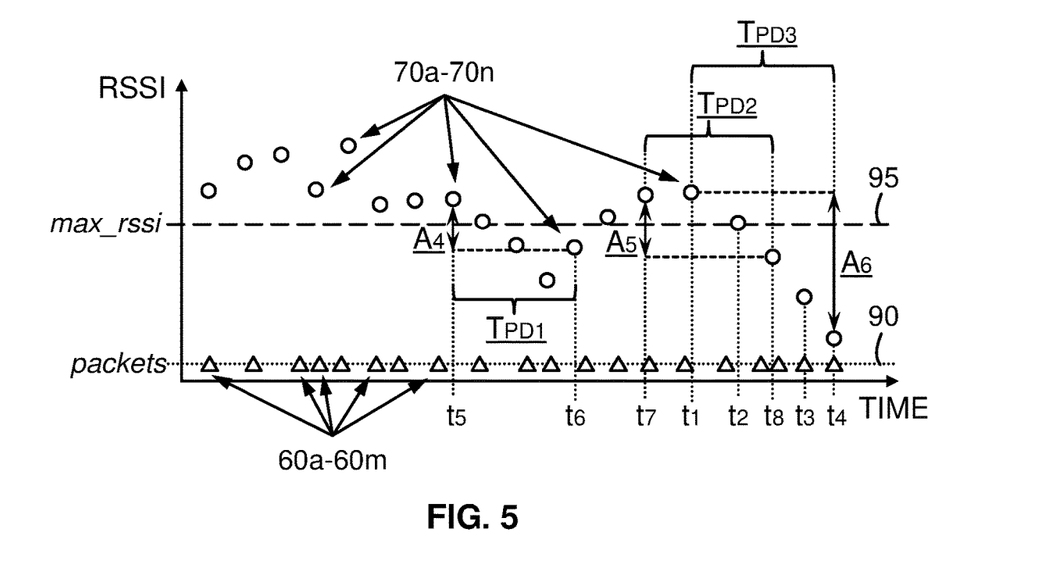

FIGS. 4 and 5 illustrate exemplary charts with measurements by the computing device of signal strength of the wireless communications connection with one sensor of the plurality of sensors of a motion tracking system.

In the chart of FIG. 4 there are illustrated a plurality of discrete values 70a-70n (illustrated as circles) corresponding to signal strength values, in particular RSSI, that have been measured by a computing device in a wireless communication connection between the device and one sensor. The values 70a-70n may be measured and stored at regular intervals, but this is not a necessary condition, i.e. they may be measured and stored for example when packets are received from the sensors (which not necessarily occurs at regular intervals). For the sake of clarity, the values 70a-70n are plotted versus time so as to illustrate the evolution of the signal strength that is to be carried out by a computing device.

While values 70a-70n are measured and stored, the wireless communications connection is established, something that in FIG. 4 does not occur after a time instant $t_4$, which may or may not coincide with the reception of a packet from the sensor. After a certain time period $T_D$ starting from said time instant $t_4$, a disconnection 90 event is triggered by the communications protocol at a time instant $t_D$.

In a most recent time span before that disconnection 90 event, said time span ranging for instance from a first time instant $t_1$ and a time instant $t_3$ or $t_4$, or even ranging from a time instant before the time instant $t_1$ and a second time instant $t_2$ (or the third or fourth time instants $t_3$, $t_4$), there has been a drop in the signal strength values 70a-70n. For example, in a first time duration $T_1$ (between the first and third time instants $t_1$, $t_3$), the difference between the corresponding signal strength values and, thus, the drop in RSSI is of a first amplitude $A_1$; in a second time duration $T_2$ (between the first and fourth time instants $t_1$, $t_4$), the drop in RSSI is of a second amplitude $A_2$; and in a third time duration $T_3$ (between the second and fourth time instants $t_2$, $t_4$), the drop in RSSI is of a third amplitude $A_3$.

For the computing device to determine that the cause of disconnection is due to the distance increase between the person and the computing device, for example from a first distance $D_1$ to a second distance $D_2$ as illustrated in FIGS. 2 and 3, the following set of conditions has to be met with respect to one sensor:

A) a difference between a first signal strength value measured at a time instant '$t_a$' and a second signal strength value measured at a time instant '$t_b$' is greater than or equal to a predetermined minimum signal strength drop threshold (min_rssi_drop);

B) a time elapsed between the time instants '$t_a$' and '$t_b$' is less than or equal to a predetermined maximum signal drop time threshold (max_drop_time); and C) a time elapsed between the time instant '$t_b$' and the disconnection between the computing device and the sensor is less than or equal to a predetermined maximum disconnection time threshold (max_time_after_drop).

And, in some embodiments, the following has to occur in addition to A), B) and C):

D) the time elapsed between the time instants '$t_a$' and '$t_b$' is also greater than or equal to a predetermined minimum signal drop time threshold (min_drop_time).

Accordingly, in this exemplary embodiment, based on the different signal strength values and time instants represented, the computing device would make such determination when at least one of the following sets is fulfilled:

set of conditions I:
I.1) the first amplitude $A_1$ is greater than or equal to a predetermined minimum signal strength drop threshold (min_rssi_drop), i.e. $A_1 \geq$ min_rssi_drop;
I.2) the first time duration $T_1$ is less than or equal to a predetermined maximum signal drop time threshold (max_drop_time), i.e. $T_1 \leq$ max_drop_time;
I.3) the time elapsed between the third time instant $t_3$ and the time instant of disconnection to is less than or equal to a predetermined maximum disconnection time threshold (max_time_after_drop), i.e. $t_D$-$t_3 \leq$ max_time_after_drop; and
preferably, I.4) the first time duration $T_1$ is greater than or equal to a predetermined minimum signal drop time threshold (min_drop_time), i.e. $T_1 \geq$ min_drop_time;

set of conditions II:
II.1) the second amplitude $A_2$ is greater than or equal to the predetermined minimum signal strength drop threshold, i.e. $A_2 \geq$ min_rssi_drop;
II.2) the second time duration $T_2$ is less than or equal to the predetermined maximum signal drop time threshold, i.e. $T_2 \leq$ max_drop_time;
II.3) the time elapsed between the fourth time instant $t_4$ and the time instant of disconnection to is less than or equal to the predetermined maximum disconnection time threshold, i.e. $t_D$-$t_4 \leq$ max_time_after_drop; and
preferably, II.4) the second time duration $T_2$ is greater than or equal to the predetermined minimum signal drop time threshold, i.e. $T_2 \geq$ min_drop_time;

set of conditions III:
III.1) the third amplitude $A_3$ is greater than or equal to the predetermined minimum signal strength drop threshold, i.e. $A_3 \geq$ min_rssi_drop;
III.2) the third time duration $T_3$ is less than or equal to the predetermined maximum signal drop time threshold, i.e. $T_3 \leq$ max_drop_time;
III.3) the time elapsed between the second time instant $t_2$ and the time instant of disconnection to is less than or equal to the predetermined maximum disconnection time threshold, i.e. $t_D$-$t_2 \leq$ max_time_after_drop; and
preferably, III.4) the third time duration $T_3$ is greater than or equal to the predetermined minimum signal drop time threshold, i.e. $T_3 \leq$ min_drop_time.

If any one of the sets of conditions I to III is fully met, i.e. each of the conditions 1), 2), 3) thereof is fulfilled (and, in some preferred embodiments, also the condition 4) thereof is fulfilled) for a same set, the computing device determines that the cause of disconnection is the distance increase between the person and the computing device. To this end, the computing device processes the different values (i.e. samples) within a processing window so as to check whether the conditions A), B) and C)—and, possibly D) as well—are met within the processing window. The processing window functions as a window that slides (i.e. sliding window), thereby withdrawing one or more samples (e.g. the older samples within the window) from the window and adding other one or more samples (e.g. the most recent samples present) to the window so that the conditions are constantly checked.

In the chart of FIG. 5 there are illustrated the same plurality of discrete values 70a-70n (illustrated as circles) of the chart of FIG. 4 even though the first, second and third time durations ($T_1$, $T_2$, $T_3$) and first, second and third amplitudes ($A_1$, $A_2$, $A_3$) have not been illustrated for the sake of clarity; neither the disconnection 90 event and the corresponding time period $T_D$ have been illustrated for the same reason. Additional fifth, sixth, seventh and eighth time instants, i.e. $t_5$, $t_6$, $t_7$, $t_8$, respectively, have been represented even though the subindices thereof do not imply a relative order with respect to the first to fourth time instants $t_1$-$t_4$ described with reference to the chart of FIG. 4.

In this chart, however, there is illustrated (with triangles) when the computing device received packets 60a-60m from the sensor corresponding to the signal strength values 70a-70n represented; the packets 60a-60m are represented on top of a dotted line 99 in the lower part of the chart. As it can be observed, the signal strength values 70a-70n do not necessarily match in time with the reception of the packets 60a-60m; in fact, the number of packets and the number of signal strength values does not necessarily have to be the same, i.e. there may be 'm' packets received from the sensor and 'n' signal strength values measured (obviously, 'm' and 'n' are natural numbers greater than zero). In some embodiments, 'm' and 'n' coincide. Also, in some embodiments, the signal strength values match in time with the reception of packets; to this end, the computing device measures the signal strength when the packets are received, or measures the signal strength of the wireless communications connection continuously but only stores the values corresponding to the reception of packets.

In some embodiments, the computing device processes the measurement orientations in the packets 60a-60m in parallel with the signal strength values 70a-70n so as to determine whether a drop in RSSI may be due to the heading rotation of the person rather than the aforesaid distance increase. The computing device evaluates the time evolution of the heading of the sensors by processing the orientation measurements (from which the computing devices gathers or derives the heading angle, as known in the art for different types of sensing devices, e.g. gyroscopes, accelerometers, magnetometers, etc.), and in parallel evaluates the time evolution of the signal strength for the respective sensor in order to establish that a drop in RSSI may be due to a heading rotation by the person (i.e. a rotation about a vertical axis thereof). To this end, predetermined minimum and maximum heading rotation thresholds (e.g. 90° and 270°, respectively; 120° and 240°, respectively; 135 and 225°, respectively; etc.) may be established so as to determine whether a heading rotation is excessive, meaning that they may possibly result in an RSSI drop due to the losses increase in the electromagnetic waves propagating from the sensors towards the computing device. Based on such processing, the computing device establishes how the person is behaving heading-wise and takes it into account when determining whether a connection loss or a potential connection loss that may be about to happen is not due to a distance increase between the person and the computing device.

In some other embodiments, the computing device processes the measurement orientations in the packets 60a-60m having a reception timestamp $t_{Rx\text{-}PACKET}$ (i.e. a time instant indicating when the packet was received at the computing device) together with signal strength values 70a-70n having a same or similar timestamp $t_{RSSI}$ (i.e. time instant indicating when the computing device measured the value); in the context of the present disclosure, it is considered that similar timestamps are timestamps not exceeding a predetermined time difference (max_time_diff), e.g. $|t_{Rx\text{-}PACKET} - t_{RSSI}| \leq$ max_time_diff, wherein the timestamp of packet reception may be a time prior or posterior to the timestamp of the signal strength value, so a previous or posterior RSSI can be processed together with the orientation measurement(s) of one or more packets as long as the time difference does not exceed max_time_diff. The computing device gathers or derives the headings from the orientation measurements, and by processing the time evolution of heading values and RSSI, it may establish how the person behaves heading-wise as explained in the paragraph above and use that information in the determination of the cause of the disconnection or potential connection loss being the aforementioned increase in the distance from the person to the computing device.

Further, in the same chart of FIG. 5, there is illustrated a dashed line 95 corresponding to a predetermined maximum signal strength threshold (max_rssi). Said max_rssi threshold establishes the maximum possible value that a measured signal strength may have for the computing device to consider that a connection loss may potentially occur. When at least one signal strength value 70a-70n has a value that is less than max_rssi, the computing device processes the values 70a-70n in accordance with the conditions A) and B) indicated above with reference to the chart of FIG. 4. Therefore, conditions A) and B) indicated above, and the following condition C') must be met:

C') at least the second signal strength value measured at a second time instant e.g. '$t_b$' (which has a signal strength value lower than the first signal strength value measured at a first time instant e.g. '$t_a$') is less than or equal to the predetermined maximum signal strength threshold (max_rssi).

For the computing device to determine that a sensor may get disconnected from the computing device within short due to a distance increase between the person and the computing device, using the examples set out with reference to FIG. 4, at least one of the following pairs of conditions needs to be fulfilled: I.1) and I.2); II.1) and II.2); and III.1) and III.2), and, in addition, also the respective one of I-III.3') condition needs to be fulfilled in accordance with condition C') above:

I.3'), II.3'), and III.3'): at least one of the two corresponding signal strength values 70a-70n is less than or equal to max_rssi, i.e. $RSSI_{I\text{-}III,1} \leq$ max_rssi and/or $RSSI_{I\text{-}III,2} \leq$ max_rssi, where the subindex I-III refers to the particular set of conditions I, II or III, and the subindices 1 and 2 refer to the first and second RSSI values of the corresponding pair of values.

In the first, second and third exemplary potential disconnection time periods $T_{PD1}$, $T_{PD2}$, $T_{PD3}$ illustrated, both the conditions A)—each of $T_{PD1}$, $T_{PD2}$ and $T_{PD3}$ has a duration less than or equal to max_drop_time—and C')—at least the RSSI value for the posterior time instant within each of $T_{PD1}$, $T_{PD2}$ and $T_{PD3}$ is less than or equal to max_rssi) are met, thus for determining that a possible disconnection may occur due to an increase in distance between the person and the computing device, the following must be met for one of said time periods:

a fourth amplitude $A_4$ (between first and last RSSI values of $T_{PD1}$) is greater than or equal to the predetermined minimum signal strength drop threshold, i.e. $A_4 \geq$ min_rssi_drop;

a fifth amplitude $A_5$ (between first and last RSSI values of $T_{PD2}$) is greater than or equal to the predetermined minimum signal strength drop threshold, i.e. $A_5 \geq$ min_rssi_drop; or a sixth amplitude $A_6$ (between first and last RSSI values of $T_{PD3}$) is greater than or equal to the predetermined minimum signal strength drop threshold, i.e. $A_6 \geq$ min_rssi_drop.

Additionally, in some embodiments, the preferable condition I-III.4)—i.e. condition D) above-described with reference to the chart of FIG. 4 is also to be fulfilled in the sets of conditions for determining that the cause of a potential disconnection to occur is due to the aforesaid distance increase.

The computing device processes the different values (i.e. samples) within a processing window so as to check whether the conditions A), B) and C')—and, possibly D) as well—are met within the processing window, which functions as a sliding window that moves one or more than one sample at a time (e.g. two, three, or more samples).

As indicated above, the orientation measurements included in the packets received at the computing device from some or all sensors may also be used in the determination for the cause of a potential disconnection that may be about to happen between one sensor and the computing device.

Even though the charts of FIGS. 4 and 5 illustrate the signal strength values and packets received from one sensor, it is readily apparent that the computing device provides similar data for each and every one of the sensors of the motion tracking system for which a wireless communications connection has been established. In this sense, the provision of one or more user perceptible signals concerning the determination made by the computing device is, in some embodiments, made with the proviso that the computing device has determined that the cause of disconnection (or the cause of a potential disconnection to occur within short) is the aforementioned distance increase for at least a number N of sensors of the motion tracking system, where N is equal to or greater than a predetermined sensors threshold (min_sensor_perc), i.e. N≥min_sensor_perc, thereby avoiding false positive determinations if fewer sensors have apparently lost connection or are about to lose connection due to the aforementioned distance increase.

Figure 6:
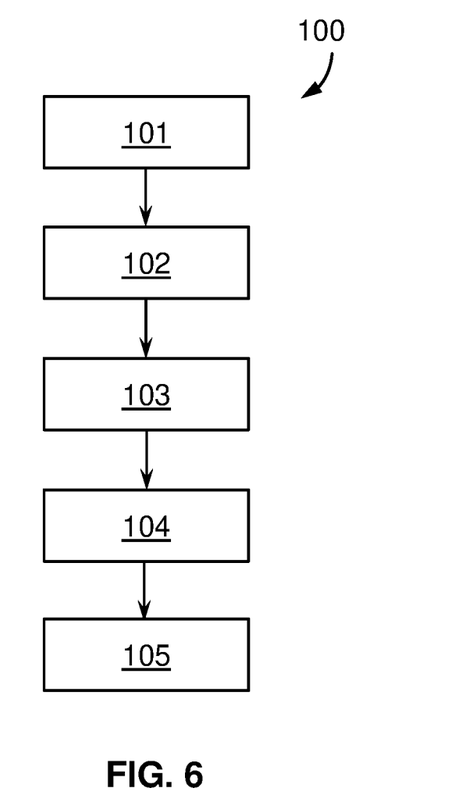
FIG. 6 diagrammatically shows a method in accordance with an embodiment.

FIG. 6 diagrammatically shows a method 100, in accordance with an embodiment, for determining cause of a disconnection between a computing device (e.g. the computing device 40 of FIG. 1) of a motion tracking system (e.g. the system 10 of FIG. 1) and one or more sensors of a plurality of sensors (e.g. one, some or all sensors 20a-20n of FIG. 1) of the motion tracking system.

A person arranges the plurality of sensors on her/his body so that the motion of the body members with sensors thereon is tracked.

The method 100 comprises a step 101 of establishing a wireless communications connection between the computing device and each sensor of the plurality of sensors. To this end, each of the computing device and the sensors are provided with a communications module for wireless data communications using a wireless communications protocol such as Bluetooth; the data is typically transmitted in the form of packets. Either the computing device or the sensors attempt to pair with the other so as to establish the connection as known in the art.

The method 100 further comprises a step 102 whereby the computing device receives a plurality of packets from each sensor of the plurality of sensors through the respective wireless communications connection. The packets typically contain one or more measurements of sensing devices of the sensor, for example orientation measurements that may have been processed by the sensor itself by the time they are sent to the computing device (e.g. with sensor fusion algorithms known in the art), or raw measurements are sent to the computing device, which in turn processes them to derive the orientation measurements for providing a movement sequence.

The method 100 further comprises a step 103 whereby the computing device measures a signal strength of the wireless communications connection with each sensor of the plurality of sensors while the wireless communications connections are established. In this sense, the computing device may obtain received signal strength indicators, i.e. RSSI, for each sensor that corresponds to the signal strength with which it receives communications from said sensor. The computing device may continuously measure the strength of the signal and store discrete values thereof, e.g. discrete RSSI values, or measure the strength of the signal with a given frequency (not necessarily at regular intervals) and store the discrete values thereof; regarding the latter, for example but without limitation, the computing device may measure the strength of the signal upon reception of packets from the sensor. In preferred embodiments, both the reception step 102 and the signal strength measuring step 103 take place simultaneously, i.e. in parallel, accordingly the computing device measures 103 the signal strength while receiving 102 the data packets.

The method 100 further comprises a step 104 whereby the computing device digitally processes the signal strength values, e.g. RSSI values, corresponding to a sensor of the plurality of sensors when said sensor has been disconnected from the computing device in order to determine if said sensor has been disconnected from the computing device because there has been an increase in the distance or gap between the person wearing the sensors and the computing device.

The measuring and processing steps 103, 104 are, thus, repeated for each sensor that is connected with the computing device.

The method 100 further comprises a step 105 whereby the computing device provides or commands the provision of at least one user perceptible signal when the computing device has determined in step 104 that at least one sensor of the plurality of sensors has been disconnected from the computing device due to a distance increase between the person and the computing device or, in some embodiments, that some or all sensors of the plurality of sensors have been disconnected from the computing device due to said distance increase.

In some embodiments, the computing device also processes the orientation measurements provided by some or all sensors of the plurality of sensors in order to make the determination of step 104 as explained above with reference to FIG. 5.

In some embodiments, as explained above with reference to FIG. 5, the method further comprises a step whereby the computing device processes the signal strength values (and, in some cases, orientation measurements as well) as described with reference to step 104 but in order to determine whether one or more sensors may get disconnected from the computing device within short because the distance or gap between the person wearing the sensors and the computing device increases.

In this text, the terms first, second, third, etc. have been used herein to describe several devices, elements or parameters, it will be understood that the devices, elements or parameters should not be limited by these terms since the terms are only used to distinguish one device, element or parameter from another. For example, the first time instant as well be named second time instant, and the second time instant could be named first time instant without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. A method for determining cause of a disconnection between a computing device of a motion tracking system and a sensor of the motion tracking system that tracks a body of a person, the computing device being configured to at least receive data through a wireless communications connection and the sensor being configured to at least transmit data through the wireless communications connection, the method comprising:

establishing the wireless communications connection between the computing device and the sensor;

receiving, by the computing device, a plurality of packets from the sensor through the wireless communications connection;

measuring, by the computing device, a signal strength of the wireless communications connection with the sensor while the wireless communications connection is established;

processing, by the computing device, signal strength values corresponding to the sensor when the sensor has been disconnected from the computing device so as to determine that the sensor has been disconnected from the computing device due to a distance increase between the person and the computing device, wherein the determination that the sensor has been disconnected from the computing device due to the distance increase between the person and the computing device is based on determining that:

a difference between a first signal strength value measured at a first time instant and a second signal strength value measured at a second time instant is greater than or equal to a predetermined minimum signal strength drop threshold, the second time instant being after the first time instant, and the second signal strength value being less than the first signal strength value, a time elapsed between the first time instant and the second time instant is less than or equal to a predetermined maximum signal drop time threshold, and a time elapsed between the second time instant and the disconnection between the computing device and the sensor is less than or equal to a predetermined maximum disconnection time threshold; and providing or commanding, by the computing device, provision of at least one user perceptible signal when the computing device has determined that the sensor has been disconnected from the computing device due to the distance increase between the person and the computing device.

2. The method of claim 1, wherein the sensor is one of a plurality of sensors, and wherein the computing device provides or commands the provision of the at least one user perceptible signal when the computing device has determined that some or all sensors of the plurality of sensors have been disconnected from the computing device due to the distance increase between the person and the computing device.

3. The method of claim 1, wherein the computing device determines that the sensor has been disconnected from the computing device due to the distance increase between the person and the computing device further when the time elapsed between the first time instant and the second time instant is greater than or equal to a predetermined minimum signal drop time threshold.

4. The method of claim 1, further comprising:
processing, by the computing device, the signal strength values corresponding to the sensor when the sensor is connected to the computing device so as to determine that the sensor may lose connection with the computing device due to the distance increase between the person and the computing device; and providing or commanding, by the computing device, the provision of at least one user perceptible signal when the computing device has determined that the sensor may lose connection with the computing device due to the distance increase between the person and the computing device.

5. The method of claim 4, wherein the computing device determines that the sensor may lose connection with the computing device due to the distance increase between the person and the computing device when:
a difference between one signal strength value measured at one time instant and another signal strength value measured at another time instant is greater than or equal to the predetermined minimum signal strength drop threshold, the another time instant being after the one time instant, and the another signal strength value being less than the one signal strength value; and a time elapsed between the one time instant and the another time instant is less than or equal to the predetermined maximum signal drop time threshold.

6. The method of claim 1, wherein the computing device processes both the signal strength values corresponding to the sensor and orientation measurements included in the plurality of packets received from the sensor when the sensor has been disconnected from the computing device so as to determine that the sensor has been disconnected from the computing device due to the distance increase between the person and the computing device.

7. The method of claim 6, wherein the computing device determines that the sensor has been disconnected from the computing device due to the distance increase between the person and the computing device further based on determining that:
a difference between headings of orientation measurements in a first packet and a second packet received from the sensor are indicative of the person not having turned more than 90° about a vertical axis thereof, the first packet and the second packet having been received by the computing device at a first reception time instant and a second reception time instant, respectively, time differences between the first time instant and the first reception time instant and between the second time instant and the second reception time instant being less than or equal to a predetermined time difference, the second reception time instant being after the first reception time instant.

8. The method of claim 1, wherein the computing device is remote from the person.

9. A motion tracking system comprising:
a sensor to track a body of a person; and
a computing device;
the sensor being configured to establish a wireless communications connection and to at least transmit data through the wireless communications connection; and
the computing device being configured to establish the wireless communications connection and to at least receive data through the wireless communications connection, and comprising at least one processor and at least one memory, the at least one memory being configured, with the at least one processor, to at least cause the computing device to perform operations comprising:
establishing the wireless communications connection with the sensor;
receiving a plurality of packets from the sensor through the wireless communications connection;
measuring a signal strength of the wireless communications connection with the sensor while the wireless communications connection is established;
processing signal strength values corresponding to the sensor when the sensor has been disconnected from the computing device so as to determine that the sensor has been disconnected from the computing device due to a distance increase between the person and the computing device, wherein the determination that the sensor has been disconnected from the computing device due to the distance increase between the person and the computing device is based on determining that:
a difference between a first signal strength value measured at a first time instant and a second signal strength value measured at a second time instant is greater than or equal to a predetermined minimum signal strength drop threshold, the second time instant being after the first time instant, and the second signal strength value being less than the first signal strength value,
a time elapsed between the first time instant and the second time instant is less than or equal to a predetermined maximum signal drop time threshold, and
a time elapsed between the second time instant and disconnection between the computing device and the sensor is less than or equal to a predetermined maximum disconnection time threshold; and
providing or commanding provision at least one user perceptible signal when it has been determined that the sensor has been disconnected due to the distance increase between the person and the computing device.

10. The motion tracking system of claim 9, wherein the sensor is one of a plurality of sensors, and wherein the provision or commanding of provision of the at least one user perceptible signal takes place when it has been determined that some or all sensors of the plurality of sensors have been disconnected from the computing device due to the distance increase between the person and the computing device.

11. The motion tracking system of claim 9, wherein the determination that the sensor has been disconnected from the computing device due to the distance increase between the person and the computing device is further based on the time elapsed between the first time instant and the second time instant being greater than or equal to a predetermined minimum signal drop time threshold.

12. The motion tracking system of claim 9, wherein the at least one memory is configured, with the at least one processor, to at least cause the computing device to perform operations comprising:
   processing the signal strength values corresponding to the sensor when the sensor is connected to the computing device so as to determine that the sensor may lose connection with the computing device due to the distance increase between the person and the computing device; and
   providing or commanding provision at least one user perceptible signal when it has been determined that the sensor may lose connection with the computing device due to the distance increase between the person and the computing device.

13. The motion tracking system of claim 12, wherein the determination that the sensor may lose connection with the computing device due to the distance increase between the person and the computing device is when:
   a difference between one signal strength value measured at one time instant and another signal strength value measured at another time instant is greater than or equal to the predetermined minimum signal strength drop threshold, the another time instant being after the one time instant, and the another signal strength value being less than the one signal strength value; and
   a time elapsed between the one time instant and the another time instant is less than or equal to the predetermined maximum signal drop time threshold.

14. The motion tracking system of claim 9, wherein the computing device processes both the signal strength values corresponding to the sensor and orientation measurements included in the plurality of packets received from the sensor when the sensor has been disconnected from the computing device so as to determine that the sensor has been disconnected from the computing device due to the distance increase between the person and the computing device.

15. The motion tracking system of claim 14, wherein the determination that the sensor has been disconnected from the computing device due to the distance increase between the person and the computing device is further based on determining that:
   a difference between headings of orientation measurements in a first packet and a second packet received from the sensor are indicative of the person not having turned more than 90° about a vertical axis thereof, the first packet and the second packet having been received by the computing device at a first reception time instant and a second reception time instant, respectively, time differences between the first time instant and the first reception time instant and between the second time instant and the second reception time instant being less than or equal to a predetermined time difference, the second reception time instant being after the first reception time instant.

16. The motion tracking system of claim 9, wherein the wireless communications connection is a Bluetooth communications connection.

17. The motion tracking system of claim 9, wherein the sensor comprises a gyroscope.

18. A non-transitory computer-readable storage medium comprising instructions which, when executed by a computing device, cause the computing device to at least perform operations comprising:
   establishing a wireless communications connection with a sensor that tracks a body of a person;
   receiving a plurality of packets from the sensor through the wireless communications connection;
   measuring a signal strength of the wireless communications connection with the sensor while the wireless communications connection is established;
   processing signal strength values corresponding to the sensor when the sensor has been disconnected from the computing device so as to determine that the sensor has been disconnected from the computing device due to a distance increase between the person and the computing device, wherein the determination that the sensor has been disconnected from the computing device due to the distance increase between the person and the computing device is based on determining that:
      a difference between a first signal strength value measured at a first time instant and a second signal strength value measured at a second time instant is greater than or equal to a predetermined minimum signal strength drop threshold, the second time instant being after the first time instant, and the second signal strength value being less than the first signal strength value,
      a time elapsed between the first time instant and the second time instant is less than or equal to a predetermined maximum signal drop time threshold, and
      a time elapsed between the second time instant and disconnection between the computing device and the sensor is less than or equal to a predetermined maximum disconnection time threshold; and
   providing or commanding provision of at least one user perceptible signal when the computing device has determined that the sensor has been disconnected from the computing device due to the distance increase between the person and the computing device.

19. The non-transitory computer-readable storage medium of claim 18, wherein the computing device determines that the sensor has been disconnected from the computing device due to the distance increase between the person and the computing device further when the time elapsed between the first time instant and the second time instant is greater than or equal to a predetermined minimum signal drop time threshold.

20. The non-transitory computer-readable storage medium of claim 18, wherein the computing device processes both the signal strength values corresponding to the sensor and orientation measurements included in the plurality of packets received from the sensor when the sensor has been disconnected from the computing device so as to determine that the sensor has been disconnected from the computing device due to the distance increase between the person and the computing device.

* * * * *